(12) United States Patent
Haenke

(10) Patent No.: US 6,841,570 B2
(45) Date of Patent: Jan. 11, 2005

(54) MATERIALS AND METHODS FOR CONTROLLING WOOD-BORING INSECTS

(76) Inventor: Jodi Haenke, 3962 Crayrich St., Orlando, FL (US) 32939

( * ) Notice: Subject to any disclaimer, the term of this patent is extended or adjusted under 35 U.S.C. 154(b) by 0 days.

(21) Appl. No.: 10/410,515

(22) Filed: Apr. 8, 2003

(65) Prior Publication Data

US 2004/0024054 A1 Feb. 5, 2004

Related U.S. Application Data

(60) Provisional application No. 60/370,650, filed on Apr. 8, 2002.

(51) Int. Cl.[7] .......................... A01N 43/16; A01N 35/06
(52) U.S. Cl. ................. 514/456; 514/919; 424/195.1; 424/DIG. 11
(58) Field of Search ............................. 514/456, 919; 424/195.1, DIG. 11

(56) References Cited

U.S. PATENT DOCUMENTS 6,524,605 B1 * 2/2003 Coats et al. ................. 424/408

OTHER PUBLICATIONS

Peterson et al. << Catnip Essential Oil as a Barrier to Subterranean Termites (Isoptera: Rhinotermitidae) in the Laboratory. J. Econ. Entomol. 96(4): 1275–1282. 2003.*

* cited by examiner

Primary Examiner—S. Mark Clardy
(74) Attorney, Agent, or Firm—Timothy H. Van Dyke; Joseph Fischer

(57) ABSTRACT

Disclosed herein or novel, environmentally friendly compositions and methods for treating or preventing infestation by termites and/or other wood-boring insects. Specifically exemplified herein are compositions containing nepetalactone, and analogs and derivatives of nepetalactone, and methods of using same.

8 Claims, 2 Drawing Sheets

MATERIALS AND METHODS FOR CONTROLLING WOOD-BORING INSECTS

CROSS REFERENCE TO OTHER APPLICATIONS

This application claims priority under 35 U.S.C. 119(e) to U.S. Provisional application, Ser. No. 60/370,650, filed Apr. 8, 2002.

BACKGROUND OF THE INVENTION

Termites cause substantial damage to residential and commercial buildings in the United States. It has been estimated that the annual cost for controlling termites and repairing their damage in the United States exceeds $1.7 billion. Subterranean termites, the most destructive of all termites, account for 95 percent of this damage. Shripat T. Kamble, internet publication, (http://www.ianr.unl.edu/pubs/insects/g1260.htm).

Subterranean termites most often enter structures from the surrounding soil to feed on wood, or other cellulosic material, of the structure and its contents. Subterranean termites construct an extensive foraging gallery beneath the soil surface. A single colony may contain several million termites with foraging territory extending up to 300 feet (Su, N.Y., R. H. Scheffrahn [1988] Sociobiol. 14(2):353–359). Since subterranean termites are cryptic creatures, their presence is not normally known until after some damage, foraging tubes, or live termites such as swarmers, are found. Some subterranean termites are known to forage beneath an object on the soil surface (Ettershank, G., J. A. Ettershank, W. G. Whitford [1980] Environ. Entomol. 9:645–648).

Control methods for structural infestations of termites varies with the ecology of the different species. Currently, there are two basic approaches for the control of subterranean termites: preventive control and remedial control. In general, preventive measures include the use of wood treated with various repellant chemicals; metal shields between the foundation supports and buildings that either act as barriers, or as a detection method when termites construct visible tubes around the shields; and the creation of chemical barriers by treating the soil under the building foundation, before and after construction, with long-residual termiticides. A layer of basaltic rock particles placed under foundations has been used as a physical barrier to stop the penetration of subterranean termite tunneling. Removal of lumber scraps and sites that accumulate water also discourages the establishment of termite colonies.

Remedial control methods can entail removal of infested wood and replacement with treated wood; drilling and injecting termiticides into small, localized infestations; fumigation of structures with widespread infestations; and use of slow-acting termiticides (Su, N.-Y., M. Tamashiro, and M. I. Haverty (1987) J. Econ Entomol. 80:1–4). Some success has been observed in treating aerial colonies of C. formosanus by the removal of their moisture source. Post-construction soil application of termiticides to eliminate subterranean termite colonies, while commonly attempted, is of limited success (Su, N.-Y., and R. H. Scheffrahn (1990a) J. Econ. Entomol. 83:1918–1924).

In some of the United States, it is mandatory that the soil underlying the foundation of newly constructed buildings be pre-treated with a termiticide to prevent termite infestation. Termiticide is typically sprayed over and into the soil prior to construction. This pre-construction treatment produces a horizontal barrier beneath the building. Because of the lack of communication between pesticide applicator and construction workers, the barrier often loses its continuity during the construction. Moreover, the currently available soil termiticides tend to lose their biological activity after five or more years to the extent that the treated soil is no longer effective against termite invasion. Established termite colonies in the soil may then invade the structure if additional chemical is not applied beneath and around the structure.

When a house or other building is infested by subterranean termites, efforts are made to create a continuous barrier beneath the building in the soil where the subterranean termites are provided access to the building. A common method of creating this barrier is to introduce termiticide around a building foundation by injection into soil underlying concrete foundations, drenching the soil surrounding the building perimeter, or a combination of both. This type of post-construction treatment is labor-intensive and may not adequately produce a continuous barrier (Frishman, A. M., B. L. Bret [1991] Pest Control 59(8):48, 52, 54, 56; Frishman, A. M., A. St. Cyr [1988] Pest Control Technology 16(4):33, 34, 36).

Other remedial treatments include spot treatments such as dusting or injecting termiticides within the walls of the building. Robert Verkerk has described arsenic trioxide dust treatment using termite lures (Verkerk, R. [1990] Building Out Termites, Pluto Press Australia Limited, P.O. Box 199, Leichhardt, NSW 2040). Verkerk describes the use of stakes or blocks of termite susceptible timber to lure termites after the stakes or blocks have been placed near a known termite problem. Once termite activity is observed, arsenic trioxide is injected. Alternatively, a portion of the termites may be dusted with arsenic trioxide.

The effectiveness of the former standard soil termiticides, chlordane and heptachlor, precluded substantial research in alternative termite control methods. Since their withdrawal from the market in 1987, replacement termiticides include chlorpyrifos (Dursban TC) and isofenphos (Pryfon 6), cypermethrin (Demon TC), permethrin (Dragnet FT), fenvalerate (Tribute) and imidacloprid(Premise). Given the loss of chlordane and heptachlor, alternative control measures, such as the use of toxicant and insect growth regulator baits, are being researched (Su, N.-Y., and R. H. Scheffrahn (1990b) Sociology 17:313–328). Concern has been raised about the use of such termiticides, due to their known toxicity. However, because of the devastation termites can cause, and the lack of less toxic, viable alternatives, the EPA has made exemptions for the use of these chemicals as termiticides, despite their known toxicity.

Chemicals used to treat wood for prevention of termite infestation include metallic salts such as mercuric chloride, copper chloride, zinc chloride, ferrous sulphate, wood tar creosote, and coal creosote. Other commonly used wood treatments include arsenic salts. All of the foregoing are known toxic chemicals, and as such are declining in use. As with chemicals used for soil treatments, very few less toxic alternatives exist. Accordingly, there is a substantial need for less toxic alternatives for preventing and treating termite infestation, as well as infestations by other wood-boring insects including, but not limited to, carpenter ants, carpenter bees, and powderpost beetles.

SUMMARY OF THE INVENTION

The subject invention is based on the inventor's discovery that nepetalactone, an oil found in Nepeta cataria (commonly known as catnip), has a dramatic repellant effect on termites. The inventor has also found that at certain concentrations, nepetalactone is lethal to termites.

Therefore, one aspect of the invention pertains to a novel composition comprising nepetalactone and formulated for treatment and prevention of termite infestation.

A further aspect of the subject invention relates to novel methods of preventing infestation of termites that comprises applying a nepetalactone containing composition on or near a structure desired to be protected. Those skilled in the art will realize that structures include, but are not limited to, posts, beams, boards, panels, sheets, and poles made out of wood or wood-based material, as well as houses and buildings made of wood and wood-based materials.

According to another aspect, the subject invention pertains to methods of treating a structure infested with termites

DESCRIPTION OF PREFERRED EMBODIMENTS

Figure 1:
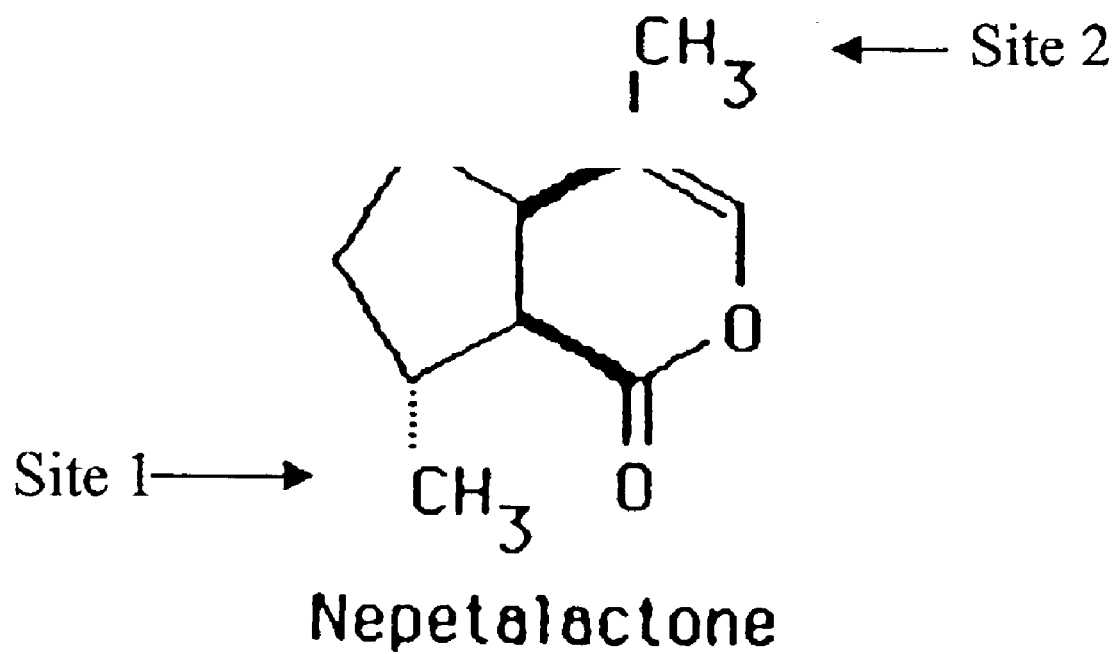
FIG. 1 shows the molecular structure of an unmodified nepetalactone molecule, pointing out the two methyl side groups.

Catnip, *Nepeta cataria*, is a member of the mint or Labiatae family. This perennial herb is sometimes known as catnip, catrup, catwort, cataria, or catmint (although there are other plants that also go by these common names). Catnip is indigenous from the eastern Mediterranean region to the eastern Himalayas, but is naturalized over much of North America and is easily grown in most gardens. The generic name *Nepeta* is said to have been derived from the Italian town Nepete, where catnip was once cultivated. For centuries humans have grown catnip for humans, but the herb is best known for its action on cats. Nepetalactone is a terpenoid composed of two isoprene units, with a total of ten carbons. Its chemical structure is similar to that of the valepotriates derived from the herb valerian, which is a mild central nervous system sedative (or stimulant to some persons).

Accordingly, the term "nepetalactone" as used herein refers to, but is not limited to, crude catnip, the oil obtained from Nepeta cataria, 5,6,7,7a-tetrahydro-4,7-dimethyl cyclopenta[c]pyran-1-(4aH)-one, and isomers, analogs and derivatives thereof, nepetic acid, nepetalic acid, (4aS,7S, 7aR)-nepetalactone, (1R,4aS,7S,7aR)-nepetalactol, cis/trans nepetalactone, and neptalactone-derived compounds whereby nepetalactone is a precursor, intermediate or reagent in forming said nepetalactone-derived compounds. Further, specific substitution of reactive constituents on or emanating from the two rings of nepetalactone may include one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, aralkyl, heteroaryl, carbocycle, or heterocycle group or moiety, or $CO_2$ $R^7$ where $R^7$ is hydrogen or $C_1$–$C_9$ straight or branched chain alkyl or $C_2$–$C_9$ straight or branched chain alkenyl group or moiety. In addition, neptalactone-derived compounds may include a pharmaceutically acceptable salt, ester, or solvate thereof. Furthermore, based on the teachings herein, those skilled in the art will appreciate the value of isolating genes responsible for the biosynthesis of nepetalactone. Therefore, nepetalactone may be recombinantly produced utilizing known genetic manipulation and molecular and cell biology techniques. It is intended that recombinantly produced nepetalactone can be used as a termite and other wood-boring insect repellant and insecticide in accord with the teachings herein. As used herein, wood-boring insects refers to, but is not limited to, all species of termites, carpenter ants, carpenter bees, and powderpost beetles. Wood-boring insects are considered different than phytophagous insects, which, in contrast to the largely cellulose-eating or -boring habits of the wood-boring insects (a sub-group of which contains symbiotic gut fauna with cellulytic enzymes), eat leaves and stems of, or suck or otherwise ingest the plant fluids from the green growth of living plants.

A knowledge of organic synthetic reactions provides a basis for modifications of natural nepetalactone compounds to obtain analogs and/or derivatives. For example, but not to be limiting, the knowledge found in the text entitled "Organic Chemistry, $2^{nd}$ edition" by John McMurry, Brooks/Cole Publishing Co., 1988, can be applied to make such modifications.

The term "alkyl" as used herein refers to straight- or branched-chain saturated aliphatic hydrocarbon groups, i.e., methyl, ethyl, propyl, i-propyl, n-butyl, s-butyl and t-butyl, the amyls, the hexyls and the heptyls.

The term "alkoxy" as used herein refers to a straight- or branched-chain saturated aliphatic hydrocarbonoxy group, i.e., methoxy, ethoxy, propoxy, 1-propoxy, n-butoxy, 1-butoxy, s-butoxy, and t-butoxy.

The term "halo" as used herein refers to chloro, bromo, and other halogens.

As used in this disclosure, the term "effective repellant concentration" is defined to indicate a concentration at which nepetalactone works to repel a designated species and/or stage and/or type (e.g., worker) of termite in a given application. The longevity of such effect may be extended by means known in the art, including but not limited to: emulsions, encapsulation, microencapsulation; mixing with carriers; mixing with preservatives; and applying into areas and/or devices that have limited exposure to the elements and/or a limited egress for the evaporative loss of nepetalactone.

As used in this disclosure, the term "effective toxic concentration" is defined to indicate a concentration at which nepetalactone is lethal to a designated species and/or stage and/or type (e.g., worker) of termite in a given application over a specified time period. Lethality is typically measured in terms of the $LD_{50}$, which is defined as the Lethal Dose, or concentration, at which half of the organisms die within a given period (such as 4, 6, 10, 16, 24, 48, or 96 hours).

In one method, nepetalactone is combined with a carrier containing a preservative, and is applied along the outside perimeter of a building structure in need of repelling subterranean termites. Preferably, a trench is dug around and near the structure, the nepetalactone in the carrier mixture is uniformly dispersed to attain an effective repellant concentration along the structure perimeter, and soil is replaced over the nepetalactone carrier mixture to cover it. In another preferred embodiment, nepetalactone is microencapsulated by any of the many methods of microencapsulation known to those skilled in the art of microencapsulation. Preferably, the microencapsulation method is chosen to allow a slow release of nepetalactone. Optionally the microencapsulated nepetalactone is mixed with a carrier, or applied in a liquid suspension, and is preferably uniformly dispersed, as described immediately above, into a trench around a building at an effective repellant concentration to provide suitable protection from subterranean termites.

It is noted that two common issues with natural, plant-derived insect repelling compounds are that 1) such natural compounds tend to be volatile, and 2) such natural compounds tend to have relatively short half lives when exposed to typical environments, such as soil containing soil microbes. Appropriately designed and synthesized analogs and/or derivatives are produced to improve the properties with regard to volatility and stability (particularly in soil). In general, the following references serve as guides for designing and synthesizing several groups of such appropriately designed and synthesized analogs and/or derivatives: U.S. Pat. No. 4,389,237 (particularly dealing with dry soil conditions and the use of Lewis acids in combination with an agent); and U.S. Pat. No. 4,412,855.

A carrier in the present context is any material with which nepetalactone is formulated to facilitate application to the locus, or storage, transport or handling. A carrier can be a solid or a liquid, including a material which is normally gaseous but which has been compressed to form a liquid. Any of the carriers normally used or known to be usable in formulating insecticidal compositions may be used.

Compositions according to the invention comprise about 0.1 to 99.9% by weight active ingredient. Preferably, compositions according to the invention comprise about 0.000001 to 10.0% by weight of active ingredient, more preferably, about 0.005 to 5.0%. More preferably, the active ingredient comprises 0.01 to 1%, by weight.

Suitable solid carriers include natural and synthetic clays and silicates, for example natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulphate; ammonium sulphate; synthetic hydrated silicon oxides and synthetic calcium or aluminum silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable. Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone. Mixtures of different liquids are often suitable, for example a mixture of isophorone with a polar organic solvent such as N-methylpyrrolidone, as are mixtures of solid and liquid carriers.

Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surface-active agent. For example, the composition may contain at least two carriers, at least one of which is a surface-active agent. A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfonated castor oil, and sodium alkylaryl sulfonates such as dodecylbenzene sulfonate; and polymers of ethylene oxide and copolymers of ethylene oxide and propylene oxide.

Compositions can, for example, be formulated as wettable powders, dusts, granules, baits, solutions, emulsifiable concentrates, emulsions, suspension concentrates, and aerosols. Compositions can be encapsulated or microencapsulated, preferably to effect slow, controlled release of the active ingredient. Wettable powders preferably contain 0.005, 0.05, 0.5, 1.0, 5.0, 10.0, 15.0, 20.0, 30.0, 40.0, 50.0, or 75% weight of active ingredient and preferably contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.005–10% weight of active ingredient, preferably 0.05 to 5%.

Granules are usually prepared to have a size between 10 and 100 BS mesh (1.676–0.152 mm), and may be manufactured by, for example, agglomeration or impregnation techniques. Generally, granules will comprise about 0.001–75% (preferably 0.05 to 20%) weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent.

Baits are prepared by, for example, combining a mixture of a finely divided cellulose material, such as sawdust, with an amount of ingredient(s) sufficient to provide the desired result; for example, from about 0.01% to about 20% weight, preferably about 0.02 to about 5%, active ingredient(s) and forming the mixture into a paste by the addition of about 1% to 5% of a water based binder such as agar. The paste-like mixture is packed into a housing such as a hollowed out wooden dowel. Baits are a preferable embodiment of the present invention. However, certain limitations as to repellancy must be dealt with when nepetalactone compounds are used in baits. The active nepetalactone compound(s) are modified to reduce repellant properties, and/or each such compound is used at a toxic level to a target organism for which such level is not repellant to that organism (i.e., the bait presents enough nepetalactone to be toxic over a period of time, but is not repellant at the level provided in the bait, or attractants in the bait outweigh and mask the repellancy of the nepetalactone compound(s) in the bait).

Wood or timber is impregnated with active ingredient according to well known procedures including pressure treatments such as the Lowery empty cell process and full cell process, vacuum treatments, hot and cold bath treatment, thermal treatment, and cold-soak treatment. Surface treatment of wood or timber is accomplished by well known techniques such as brushing, dipping, infusing, coating, spraying or short-soaking the wood material with active ingredient or appropriate compositions thereof in amounts and in a manner that would be apparent to one skilled in the art.

For instance, wood treatments may be accomplished by two major methods: impregnation of the wood through vacuum and pressure treatments and surface treatments such as painting, coating, spraying or dipping. In an impregnation method, a concentrate may be formulated which comprises about 0.01–65% weight per volume active ingredient, 5–50% solvent and, when necessary, co-solvent, and 0–40% w/v of other additives such as penetrants. For treatment, vacuum is pulled on a vessel containing the wood. The concentrate is then added to the vessel and subsequently pressurized to force concentrate into the wood. The vessel is relieved of pressure and the treated wood then removed. In a surface treatment, the concentrate may be simply painted onto a wood surface by means of brushing or spraying or, preferably, dipping. Solvents used for these types of treatments may include polyethylene glycol, and aromatic solvents, and the like due to their ability to penetrate wood.

Emulsifiable concentrates usually comprise, in addition to a solvent and, when necessary, cosolvent, about 0.01–50% weight per volume active ingredient, 2–50% weight per volume emulsifiers and 0–50% weight per volume of other additives such as stabilizers, penetrants and corrosion inhibitors.

Suspension concentrates are usually compounded so as to obtain a stable, non-sedimenting flowable product and usually comprise about 0.01–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency. Compositions can also comprise other ingredients, for example, further active compounds possessing herbicidal, insecticidal or fungicidal properties, in accordance with the requirement of the locus to be treated and the treatment method.

Other mixtures than the mixtures exemplified above may be used for application on materials such as woods, as emulsifiable concentrates, and as suspension concentrates. Preferred final composition concentrations may range from 0.000001 to 10.0 percent by weight, or more preferably from 0.005 to 5.0 percent by weight, or even more preferably from 0.01 to 1.0 percent by weight, depending on the application.

The method of applying an extract of this invention to prevent or treat infestation of termites comprises applying nepetalactone, conveniently in a composition comprising the nepetalactone of this invention and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combating termite infestation. This dosage is dependent upon many factors, including the carrier employed, the method and conditions of the application, whether the formulation is present at the locus in the form of a film, or as discrete particles or as a bait, the thickness of film or size of particles, the degree of termite infestation, the duration of persistence desired or required, and the like. Proper consideration and resolution of these factors to provide the necessary dosage of the active ingredient at the locus to be protected are within the skill of those versed in the art. In general, however, the effective dosage of the compound of the invention at the locus to be protected (i.e., the dosage to which the termite has access) is of the order of about 0.01 to 10.0% based on the total weight of the composition, preferably, about 0.2% to 5%.

In one embodiment of this invention, the compositions of this invention are used to combat termites in the soil, thereby achieving indirect protection for any wood or wood-based constructions erected on the treated soil or to crops, grassland, forestry (especially young saplings), and other cellulose based materials surrounded by or located in the treated soil. Suitable soil-based control of termites is obtained by providing in the soil an effective dosage of a composition of this invention. For use in this manner, the active ingredient is suitably applied to the soil at a rate of from about 0.001 gram to about 10 kilograms per hectare. Depending on the composition used, good control of soil inhabiting termites is obtained at rates of from about 0.001 gram to about 1 kilogram per hectare and preferably from about 0.01 gram to 100 grams per hectare. The nepetalactone of this invention can conveniently be formulated for use as an extract-impregnated wooden stake, bait, granule or powder containing a solid diluent, or as a suspension concentrate. Such formulations generally comprise from about 0.01 to about 50% by weight of the active ingredient. Effective control results when the formulation is physically integrated into the topsoil, in a trench surrounding the vulnerable site, or when it is applied to the surface of the soil. In certain embodiments, doses of nepetalactone (which is meant to include its analogs and derivatives) are applied into soil at intervals sufficient to create a vertical barrier in the soil to termites.

The compositions of this invention can also be applied as a drench, i.e., as a solution or dispersion of the compound in a suitable solvent or liquid diluent. Such drenches can be prepared by diluting with water a concentrate containing a nepetalactone of this invention, an emulsifying agent, and preferably an organic solvent, such as isophorone and/or N-methylpyrrolidone. The nepetalactone of this invention can be applied by band, furrow or side-dress techniques, and may be incorporated or not.

In another embodiment of the invention, the compositions of this invention are applied directly on or into the material to be protected or treated. For example, timber is treated either before, during or after its incorporation into a structure or building, thereby protecting it against damage from termite attack or combating an already existing infestation of termites. For treatment of timber, the composition can contain a penetrant designed to facilitate penetration of the active ingredient to a significant depth in the timber, thereby ensuring that superficial-surface abrasion will not generate a surface free from active ingredient and thus vulnerable to termite penetration. Examples of materials known for use as wood penetrants include paraffinic hydrocarbons, for instance low aromatic white spirit, 2-ethoxyethanol and methyl isobutyl ketone. Preferably the penetrant is 2-ethoxyethanol or methyl isobutyl ketone, optionally in association with isophorone and/or N-methyl pyrrolidone. It is useful in such timber treatment to incorporate "anti-bloom" agent, which counteract the tendency for the active ingredient to migrate to the surface ("blooming"), suitable materials being dibutyl phthalate and o-dichlorobenzene.

Timber treatment compositions can also, if desired, contain fungicides (to prevent fungal attacks such as dry rot and wet rot), and/or pigments in order to combine termite protection with painting of the timber. In this context, painting will be understood to include not only the application of covering pigmentation (commonly white), but also the application of natural wood coloration in order to restore the appearance of weathered timber (e.g., as with treatments to red cedar external housing timbers).

The actual application onto or into the timber may be carried out using conventional techniques including immersion of the timber in the liquid, painting the liquid onto the timber by spray or brushing, and injecting the liquid into the timber.

The concentration of active ingredient in the treated timber should, of course, be sufficient to achieve the desired effect. However, the total volume of formulated product taken up by the timber is limited by the absorption properties of the wood with respect to that formulation and will also vary according to the application procedure adopted (immersing, painting or injecting); hence the concentration of active ingredient in the formulation should be such as to produce the desired concentration in the treated timber. The formulation may be aqueous, as for example obtained by dilution of a conventional insecticide emulsifiable concentrate, or non-aqueous such as an undiluted emulsifiable concentrate. The organic solvent in such formulations will suitably be one of those previously described.

Furthermore, according to another aspect of the invention, nepetalactone is provided and formulated for conventional paint or paints of various colors and qualities, for decorating and protecting, houses, buildings, and other structures.

The determination of the necessary parameters applicable to specific types of wood and particular treatment procedures can readily be determined by established techniques conventionally used by those skilled in the art.

The following examples are provided to illustrate aspects of the invention, and are not intended to limit the scope of the invention.

EXAMPLE 1

Toxicity and Repellency of Nepetalactone Against Termites

Materials: *Reticultiermes flavipes*, from the family Rhinotermitidae, the most common subterranean termites, were collected for toxicity tests, nepetalactone was obtained by commercial purchase (Kooky Kat Catnip Co., B.C.). For repellency assays, a donated amount of nepetalactone was provided from Iowa State University, courtesy of Dr. Joel Coates.

Bioassays: Acetone was used as solvent for nepetalactone and control (permethrin). Absorbent (Fisherbrand) coarse, filter paper was treated with nepetalactone and controls and placed in standard, sterile polystyrene 100×15 mm petri dishes. *Reticultierme flavipes* (20 per replication) were placed in petri dishes and location monitored at 6 ten minute intervals.

Toxicity tests: Toxicity tests of nepetalactone were conducted to determine non-lethal percentage for repellency assays. Permethrin (0.1%) solutions served as known control. Four strengths of nepetalactone were measured: 5.35%, 0.535%, 0.0535%, and 0.000004%. Results are shown in Table 1. Based on the evident mortality, 0.0535% nepetalactone was selected as the repellency test solution.

Repellency tests: Eight trials each of 0.0535% nepetalactone, 0.1% permethrin, blank, and pure acetone solvent were ran to test repellency. Filter papers were cut in half with solvent on one half and treated side on the opposite half. Treated sides were rotated every other dish to ensure that termites did not favor a particular side of dish for extraneous reasons. Termites were measured on treated and untreated sides at six consecutive ten minute intervals. Percent repellency was calculated as follows: (# live termites–# live termites treated)/total #termites. The results of the repellency tests are shown in Table 2. Standard mean of the Error (SEM): SEM=$(variance)^{1/2}/n$.

These results show the clear repellant and toxic effects of nepetalactone to the termites tested.

EXAMPLE 2

Manufacture of One Group of Nepetalactone Derivatives

A wide range of possible analogs and derivatives of nepetalactone are useful in the present invention to repel wood-boring insects. The following examples are not meant to be limiting as to that range of possible analogs and derivatives of nepetalactone.

For instance, and not meant to be limiting, a chloroacetyl group is added to one or more of the carbon atoms of the nepetalactone molecule. In preferred embodiments, the addition is to one of the two methyl side groups of nepetalactone (see FIG. 1), identified for purposes of this example as site 1 and site 2.

Figure 2:
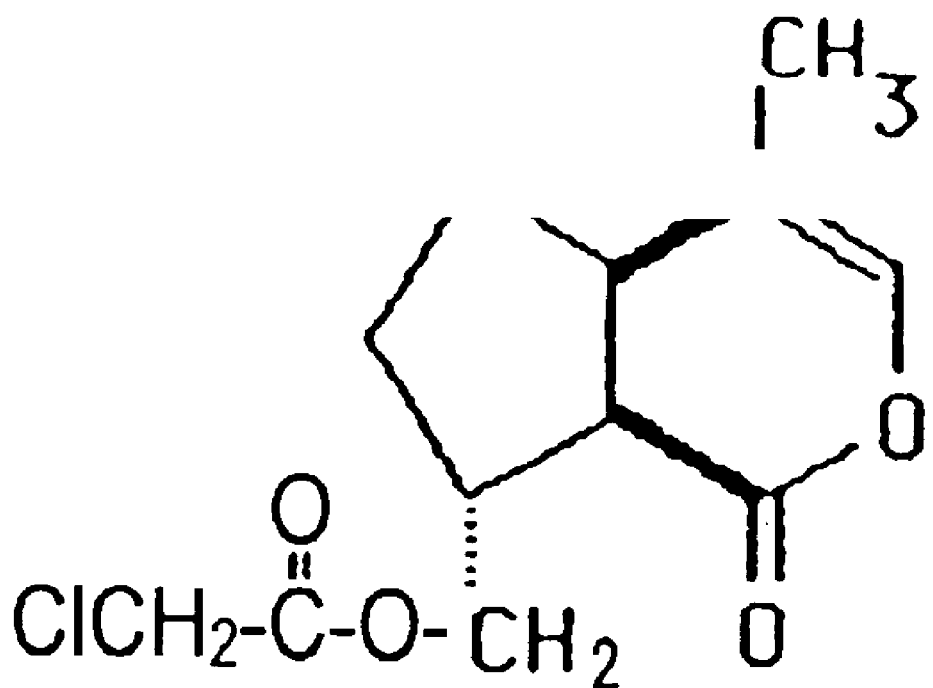
FIG. 2 shows the molecular structure of one example of a modified nepetalactone molecule, pointing out modifications of the two methyl side groups.

In one of the preferred embodiments, the methyl group at site 1 is substituted or otherwise converted to a chloroacetyl group. In another of the preferred embodiments, a chloroacetyl group is attached to the methyl group at site 1 by means of a carboxyether linkage (see FIG. 2).

In two other preferred embodiments, the above two modifications, respectively, are made at site 2, independently of one another.

In other preferred embodiments, one of the above two modifications at site 1 is made, and a substitution of a branched alkoxypropyl side chain is made at site 2. The alkoxy side chain preferably is a methyl or ethyl group, and may be attached to any position of the propyl group (where the β is preferred to the γ which is preferred to the α position).

For any of the above-described embodiments of derivatized nepetalactone compounds, a halogen other than chlorine is substituted for the chlorine so described. For any of the above-described embodiments of derivatized nepetalactone compounds, an alkyl compound other than propyl is substituted for the propyl so described (while an alkoxyl side chain remains attached thereto). In other embodiments, no alkoxyl side chain remains, only an alkyl compound side chain other than propyl in place of the propyl described above.

Such derivatives have different volatilities relative to non-derivatized nepetalactone. The effect of a lower volatility, which is expected to increase longevity of a treatment of soil against termites, may, in some cases, decrease the level of repellancy. A cost-benefit analysis of these countering trends is necessary to determine the better-performing derivatives (taking into account, also, changes in toxicity to humans and appropriate mammalian, avian, amphibian, etc. test species).

One or more of the above nepetalactone derivatives is tested, as in Example 3, below, for improvement in longevity in a soil sample (such as measured by half-life of repellancy) and for actual repellancy in the soil, as compared to a non-derivatized nepetalactone. Basic laboratory testing of toxicity and repellancy are evaluated as described in Example 1, above. The dual criteria of improvement in half-life of repellancy, while maintaining a repellant quality (i.e., the basic repellancy prior to degradation in the soil is comparable or better than non-derivatized nepetalactone in terms of the quantity needed to repel a termite), are used to select useful nepetalactone derivatives. Testing such as so described in Examples 1 and 3 is routine in the art, and is used to identify the most desirable of the derivatized nepetalactone compounds.

EXAMPLE 3

Methods of Evaluating Nepetalactone Derivatives in Soil

The following routine analytical methodologies are taken from a Study Plan entitled, "Behavioral Effects of Catnip Essential Oil on Termites in the Laboratory," by Christopher J. Peterson, Research Entomologist at the USDA Forest Service, Starkville, MS. Additional methodologies are provided in one or more of the references cited at the end of this example.

The primary purposes of the methodologies are to evaluate compounds, such as the derivitized nepetalactone compounds described in Example 2 above, and other nepetalactone analogs and derivatives, as defined and/or described herein, for stability in the soil and for endurance over time, in the soil, as termite repellants. A control compound for such evaluations is nepetalactone, and another control is the insecticide pyrethrin.

The basic, routine methodology is as follows. In a comparative test with nepetalactone compared with one or more analogs and/or derivatives of nepetalactone, multiple replicates of each are preferably evaluated. Also, each comparison is conducted with termites from at least two distinct sources given recognized variability in termite colonies.

Sand treatments. Dry sand will be treated with the appropriate amount of compound dissolved in solvent, or with solvent alone for control treatments. The sand will be treated in jars, capped and placed on ajar roller for five minutes to ensure even distribution of the compound. The sand will then be removed from the jars and placed into metal pans or glass petri dishes and allowed to air-dry in a fume hood for 15 to 30 minutes (or longer, depending on test, see below) to allow all the solvent to escape.

Toxicity Assays.

Microwell Assay. Direct application of acetone dilutions of catnip essential oil to termites will be conducted. Filter paper circles will be placed in individual wells of a 96-well microplate Five $\mu$l of distilled water will be placed in each well Termites (12) will each be treated with 0.5 $\mu$l of the appropriate acetone dilution of catnip essential oil, applied to the abdomen. Each termite will be placed into individual wells of the microplate. Each plate will be wrapped with a moist paper towel and placed in a plastic box with a lid. The boxes will be placed in an incubator at 25° C. in the dark. Mortality will be recorded at 24 hours and seven days. Three replicates will be conducted for each test, and the test will be run twice. The plates will be placed in an incubator at 25° C. and 70% RH in the dark. Five doses resulting in >0 but <100% mortality will be used to calculate $LD_{50}$ values, after correction for control mortality by Abbott's equation. $LD_{50}$ values will be calculated by using probit analysis or trimmed Spearman-Karber analysis on SAS.

Fumigation Assay. Toxicity through exposure in the vapor phase will be determined by using a fumigation assay. A 150-ml glass jar with a screw cap will be used as a fumigation chamber. A 4.25-cm diameter piece of filter paper will be placed in the bottom of the jar. Distilled water, 150 $\mu$l, will be applied to the filter paper. Twenty termite workers will be added to the jar. A second piece of 4.25-cm filter paper will be treated with 200 $\mu$l of the appropriate acetone dilution of catnip oil. The acetone will be allowed to dry for 5 minutes before being placed in the jar. When dry, the treated filter paper will be placed over the mouth of the jar, and the lid will be fastened. Three replicates per test will be conducted, and the test will be run twice. The jars will be placed in an incubator at 25° C. and 70% RH in the dark. Five concentrations resulting in >0 but <100% mortality will be used to calculate $LC_{50}$ values, after correction for control mortality by using Abbott's equation. $LC_{50}$ values will be calculated by using probit analysis on SAS.

Petri Dish Assay. Agar will be poured into 60 by 15 mm petri dishes to a depth of 2–3 mm. Treated sand (1 g) will be poured on top of the agar. Ten worker termites will be introduced into the petri dishes and the dishes will be covered. The termites will be observed at fifteen-minute intervals for 6 hours, then hourly for two additional hours, then again at 24 hours. Termite activity will be observed and rated: normal, ataxic (sluggish), moribund (immobile but living) and dead. $LC_{50}$ and $LT_{50}$ values will be calculated by probit analysis if data support calculation (for purposes of $LC_{50}$ calculation, those termites rated as "moribund" or "dead" will be considered dead). Doses of catnip oil will be: 5, 10, 25, 50, 100, 250, 500, 750, and 1000 ppm. Blank and solvent controls will be conducted. Three replicates will be conducted. Data will be transformed by arcsine of the square root and subjected to one-way ANOVA ($\alpha$=0.05), followed by least squared means comparison.

Longevity of catnip oil in sand. Excess sand from the solvent, 10, 100 and 1000 ppm doses of the toxicity test will be subjected to HPLC analysis as a check of dose. Twenty g of sand will be extracted with 20 ml methanol, filtered and injected into the HPLC for quantitation. This will serve as a check of nominal dose. A standard curve will be constructed by using HPLC of reference compound and the standard curve will be used to determine sand concentration of the oil. Jars of sand will be capped and sealed with Parafilm and stored in an incubator at 25° C. and 70% RH in the dark. At one-week intervals, 20 g portions will be removed from the jars and extracted with 20 ml methanol, followed by analysis by HPLC. Sampling will continue until the treated sand is depleted. The data will be used to determine rate of disappearance of the catnip oil, and of individual nepetalactone isomers.

Behavioral Assays.

Tunneling Assay. Three doses will be selected for use in this test, the highest dose being the highest non-toxic dose from the toxicity test. Each test apparatus will consist of a 2.5-cm diameter by 25-cm long glass test tube. A 2 by 1 by 1 cm block of southern yellow pine sapwood is placed at the bottom of the test tube. The test tube is filled with a 50:50 (vol:vol) mixture of autoclaved sand and vermiculite substrate to a depth of 6 cm, and 5.5 ml of distilled water is added. One hundred g of sand will be treated as described above with 5.5 ml acetone solution of catnip oil at the appropriate dose, requiring 5 min on the jar roller and 15 min in the fume hood for solvent evaporation. Treated sand is added to a depth of 6 cm (approx 35.5 g sand) on top of the sand-vermiculite mixture. If necessary, the sand will be lightly tamped down to eliminate air pockets in the sand.

Sand and vermiculite substrate is then added to the test tube to a depth of 6 cm and a 1.5 cm wooden cube is pressed 0.5 cm into the substrate. The top substrate is then moistened with 5.5 ml of distilled water. Eighty worker termites plus one soldier will be placed in the upper 6 cm substrate. Each tube is covered with a piece of aluminum foil, and the tubes are labeled with the appropriate test information. The test will be replicated five times for each concentration. Solvent controls will be conducted. The tubes will be placed in an incubator at 25° C. and 70% RH in the dark. After one week, the depth of tunneling and percentage mortality will be recorded The distance of sand tunneled and number of termites recovered from the tubes will be subjected to ANOVA and means compared by Tukey's honestly significant difference test.

Barrier Assay. Three doses will be selected for use in this test, the highest dose being the highest non-toxic dose from the toxicity test. A modification of Blaske and Hertel (2001) termites. This method is based on a zone of untreated sand, the "introduction zone", a "barrier zone" of treated sand, and another untreated, or "protected zone" on the other side of the introduction zone. Sand (100 g) will be treated with 20 ml of acetone dilution of the essential oil. Five minutes on the jar roller will be required to distribute the chemical evenly, and the sand will be placed in glass petri dishes in the hood for 60 minutes to allow the solvent to evaporate. Paper cards will be placed in the box (13.5 by 12.75 cm) to divide it into thirds. Once dry, 100 g of the treated sand, 100 g sand for the introduction zone and 100 g of sand for the protected zone, will be added to the boxes in a way to provide a barrier of treated sand through the middle of the box. Each section will be moistened with 20 ml of distilled water and the paper cards will be removed. Two 2 by 1 by 1 cm block of southern yellow pine sapwood will be placed in the sand in both the introduction and protected zones, and sand will be excavated around the block so that the termites will have access to the bottom of the box. The termites (200 workers plus 2 soldiers) will be placed in the introduction zone on the wood blocks. A random number table will be used to determine the position of the introduction and treated zone (to the right or the left). The boxes will be placed in an incubator at 25° C. and 70% RH in the dark. Five replicates will be conducted for each concentration and for the control. An acetone control will be run. After seven days, the termite tunnels will be examined to determine if the termites have penetrated the sand barrier. Boxes will be photocopied to document visible tunnels on the bottom of the box. Surviving termites will be excavated and counted from each of three zones in the boxes (introduction area, treated area, and termites will be counted, and when 70% of termites in any dish were dead or moribund, that concentration was ended.

Percentage repellency will be calculated by subtracting the number of termites on the treated side from the number on the untreated side, dividing that quantity by the total number present, and multiplying by 100 to convert to a percentage. A paired t-test will be used to determine if the number of termites on the treated side differed from the number on the untreated side. The model will be analyzed for significance by using ANOVA for repeated measures on SAS. protected area). The photocopied tunnels and galleries will be traced onto transparency film, photographed with a digital camera, and analyzed by ImagePro (version 3.2) for total visible area excavated. Percentage survival (total for the entire box) and percentage of area excavated will be transformed by the arcsine of the percentage and analyzed by one-way ANOVA ($\alpha=0.05$) and means compared by Tukey's honestly significant difference test.

Repellency Assay. This method follows that of Zhu et al. (2001a). Three doses will be selected for use in this test, the highest dose being the highest non-toxic dose from the toxicity test. Five replicates will be conducted. A 5-cm diameter and 1 cm high Petri dish will be filled with 1 ml of agar solution. One half of the surface of the agar will be covered with 0.5 g treated sand, and the other half of the petri dish will be covered with 0.5 g untreated sand. A piece of untreated filter paper (1 cm in diameter) will be placed on each half of the petri dish. Ten worker termites will be placed in each petri dish, and dishes will be placed in an incubator at 25° C. and 70% RH in the dark. A random number table will be used to determine the position of the treated and untreated sides (to the right of the left). Reading will be taken every 15 minutes for the first hour, then hourly for the next five hours, then every 24 hours for 24 days. Dead and moribund termites will be counted, and when 70% of termites in any dish were dead or moribund, that concentration was ended. Percentage repellency will be calculated by subtracting the number of termites on the treated side from the number on the untreated side, dividing that quantity by the total number present, and multiplying by 100 to convert to a percentage A paired t-test will be used to determine if the number of termites on the treated side differed from the number on the untreated side. The model will be analyzed for significance by using ANOVA for repeated measures on SAS.

The following references are provided and are relevant to the testing methods in Examples 1 and 3:

Blaske, V-U and H Hertel. 2001. Repellent and toxic effects of plant extracts on subterranean termites (Isoptera: Rhinotermitidae). J. Econ. Entomol. 94(5):1200–1208.

Haenke, J A, B Poetz, C Ramirez, C J Peterson and J Ems-Wilson, 2002. Effect of catnip on indigenous Florida subterranean termites *Picogram and Abstracts*, American Chemical Society, Division of Agrochemicals, 223$^{rd}$ ACS National Meeting, Apr. 7–11, 2002, Orlando, Fla. Issue #62, Spring 2002, Abstract #33.

Peterson, C J, L T Nemetz, L M Jones and J R Coats. In Press. Behavioral activity of catnip, *Nepeta cataria* (Lamiaceae), essential oil components to the German cockroach, *Blattella germanica* (Blattodea: Blattellidae). J. Econ. Entomol.

Scheffrahn, R F and N-Y Su. 1994. Keys to soldier and winged adult termites (Isoptera) of Florida. Florida Entomol. 77(4):460–474.

Zhu, BCR, G Henderson, F Chen, H Fei and R A Laine. 2001a. Evaluation of vetiver oil and seven insect-active essential oils against the Formosan subterranean termite. J. Chem. Ecol 27(8):1617–1625.

Zhu, BCR, G Henderson, F Chen, L Maistrello, and R A Laine. 2001b. Nootkatone is a repellent for the Formosan subterranean termite (*Coptotermes formosanus*). J. Chem. Ecol. 27(3):523–531.

An improved nepetalactone derivative has, preferably, an improvement of between 10 and 20,000 percent in stability in soil over non-derivatized nepetalactone, and more preferably, between 500 and 20,000 percent improvement in same, and even more preferably, between 5,000 and 20,000 percent in same. Microencapsulation or other forms of extending the stability and release of the derivatized nepetalactone compound further increases the overall useful life of the compound in soil or lumber or other applications as defined herein.

With regard to extension of useful life of a nepetalactone, or an analog or derivative of nepetalactone, encapsulation by methods described in any of the following are used to achieve this goal: U.S. Pat. Nos. 3,577,515; 4,808,206; 4,774,090; 4,954,298; 4,056,610; 5,145,675; 5,518,736; 5,225,279; 5,225,279; 6,015,570; and 6,165,615. The use of a microencapsulated form of nepetalactone, or an analog or derivative of nepetalactone, is among the preferred approaches to treating wood and wood products to repel and prevent infestation of termites, and for establishment of barriers in soil, such as around houses and other buildings containing wood or wood products that are susceptible to termite infestation and damage. The use of microencapsulated forms, or other methods of presentation, may be in combination with other approaches, such as the use of baits, the addition of boric acid, etc., as is known in the art of termite control and eradication.

Also, it is recognized that with regard to changes in volatility of an analog or derivative of nepetalactone, it is expected that with increasingly longer attached side chains, and with increasing the relative hydrophobicity (increasing intramolecular attraction), decreased volatility is expected.

All patents, patent applications and publications discussed or cited herein are understood to be incorporated by reference to the same extent as if each individual publication or patent application was specifically and individually set forth in its entirety.

Having generally described this invention, including the best mode thereof, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein. Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

What is claimed is:

1. A method of treating a structure infested with termites comprising applying a composition comprising nepetalactone to said infested structure, wherein said nepetalactone is of a effective concentration to kill or repel said termites.

2. The method of claim 1 wherein said structure comprises wood, a wood-based material, or combinations thereof.

3. The method of claim 2, wherein said structure is at least one beam, board, pole, post, or sheet, or combinations thereof.

4. The method of claim 2, wherein said structure is a house or building comprising said at least one beam, pole, board or sheet, or combinations thereof.

5. The method of claim 1 wherein said composition further comprises a carrier.

6. The method of claim 1 wherein the concentration of said nepetalactone is between about 0.005% and about 5.0%.

7. A method for preventing infestation of termites in a structure comprising digging a trench around at least a portion of said structure; applying in said trench a composition comprising nepetalactone; filling in said trench; whereby said composition forms a barrier to deter migration of termites into said structure.

8. The method of claim 7, wherein said structure is comprised of a beam, board, post, pole or sheet made of wood or a wood-based material.

* * * * *